(12) United States Patent
Cote et al.

(10) Patent No.: US 9,644,190 B2
(45) Date of Patent: May 9, 2017

(54) MODIFIED GLUCANSUCRASE AND RELATED METHODS

(71) Applicant: The United States of America, as represented by the Secretary of Agriculture, Washington, DC (US)

(72) Inventors: Gregory L. Cote, Edwards, IL (US); Christopher D. Skory, Washington, IL (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 12 days.

(21) Appl. No.: 14/606,720

(22) Filed: Jan. 27, 2015

(65) Prior Publication Data

US 2015/0218532 A1 Aug. 6, 2015

Related U.S. Application Data

(60) Provisional application No. 61/936,663, filed on Feb. 6, 2014.

(51) Int. Cl.
*C12N 9/24* (2006.01)
*C12N 9/10* (2006.01)
*C12P 19/18* (2006.01)
*C08B 37/00* (2006.01)
*C12P 19/04* (2006.01)

(52) U.S. Cl.
CPC ........ *C12N 9/1048* (2013.01); *C08B 37/0009* (2013.01); *C12P 19/04* (2013.01); *C12P 19/18* (2013.01)

(58) Field of Classification Search
CPC .................................................... C12N 9/1048
USPC ........................................................ 200/200
See application file for complete search history.

(56) References Cited

PUBLICATIONS

Accession No. Q8G9Q2 (2003).*

* cited by examiner

*Primary Examiner* — Tekchand Saidha
(74) *Attorney, Agent, or Firm* — John D. Fado; Mark D. McNemar

(57) ABSTRACT

Disclosed is a genetically modified enzyme belonging to glycosyltransferases type of glucansucrase comprising at least one mutation at position 654 of said enzyme, wherein modified enzyme is capable to producing a glucan polymer.

11 Claims, 9 Drawing Sheets

```
Sm GtfB   1→3   557 F I R A H D S E V Q D L I A D I I K A E I 577
Ss GtfJ   1→3   607 F I R A H D N N V Q D I I A E I I K K E I 627
Sd GtfI   1→3   569 F A R A H D S E V Q D L I R D I I K A E I 579
Sm GtfD   1→6   579 F I R A H D S E V Q T V I A K I I K A Q I 599
Sd GtfS   1→6   542 F I R A H D S E V Q T R I A K I I R E K L 562
Lm DsrS   1→6   657 F V R A H D S E V Q T V I A Q I V S D L Y 677
Lm DsrI   1→3   644 F V R A H D S E V Q T V I A E I I K Q R I 664
                                    △
                                   TS
```

FIG. 1

MODIFIED GLUCANSUCRASE AND RELATED METHODS

CROSS-REFERENCE TO RELATED APPLICATION

This present application claims priority under 35 U.S.C. §119(e) to U.S. Provisional Ser. No. 61/936,663, which was filed on Feb. 6, 2014, and is hereby incorporated by reference.

FIELD OF INVENTION

The present invention is related to a modified glycoside hydrolase enzyme comprising at least one mutation to the amino acid downstream from a transition state stabilizer site wherein the modified enzyme produces a glucan. The modified glucan can have a higher yield of 1,3-disubstituted α-D-glucopyranosyl units as compared to a glucan produced by a wild-type glucansucrase, a higher yield of 1,6-disubstituted α-D-glucopyranosyl units as compared to a glucan produced by a wild-type glucansucrase, lower water solubility as compared to a glucan produced by a wild-type glucansucrase, or higher water solubility as compared to a glucan produced by a wild-type glucansucrase.

BACKGROUND OF INVENTION

Glucansucrases are a type of glycosyltransferase (GTF) that belong to the glycoside hydrolase family 70 (GH70), as defined by the CAZy classification system (Cantarel B. L., et al., 2009, Nucleic Acids Res 37:D233-D238), and catalyze the transfer of D-glucopyranosyl units from sucrose to acceptor molecules to form α-glucan chains. Glucansucrases are capable of catalyzing the synthesis of several different α-glucosidic linkages that affect molecular mass, branching, and solubility of the polysaccharide. In general, α-glucans containing mostly α(1→6) linkages (e.g., dextran) are water-soluble, while those made primarily of α(1→3) linkages are water-insoluble. Sequences of α(1→6) linked glucose units tend to form a flexible chain which readily hydrates and dissolves in water, whereas sequences of α(1→3) linked glucose units tend to form extended ribbon-like helices which self-associate and are water-insoluble, similar to cellulose (Rees D A, et al., 1971, J Chem Soc 8:469-479; Yui et al., 2000, Biosci Biotechnol Biochem 64:52-60). The term "mutan" is often used to refer to the water-insoluble glucan produced by *Streptococcus mutans* and related bacteria (Guggenheim et al., 1970, Helv Odont Acta 14:89-108), and it has become well-established that "mutan" is a graft or block-type copolymer consisting of regions of dextran-like α(1→6) linkages sequences as well as sequences of α(1→3) linked regions. This block or graft copolymer structure is quite different from the highly water-soluble alternan, which has similar proportions of α(1→3) and α(1→6) linkages arranged in a regular, alternating fashion with no extended sequences of either linkage type (Côté, 2002, Chapter 13 in Biopolymers, Vol. 5. Polysaccharides I. Polysaccharides from Prokaryotes. E. J. Vandamme, S. DeBaets, A. Steinbiichel, Eds. Wiley-VCH, Weinheim, Germany. Pp. 323-350).

Whereas the utility of water-soluble dextran has been well-established (Leathers, 2002, Chapter 12 in Biopolymers, Vol. 5. Polysaccharides I. Polysaccharides from Prokaryotes. E. J. Vandamme, S. DeBaets, A. Steinbiichel, Eds. Wiley-VCH, Weiheim, Pp. 299-321), applications of the related water-insoluble glucans are much less developed. As such, there is a need to establish a range of related water-insoluble glucans with varying properties.

Three-dimensional structures and targeted modifications of glucansucrases have provided substantial information regarding the functionality of these enzymes (Vujicic-Zagar, et al., 2010, Proc Natl Acad Sci USA 107:21406-21411; Ito, et al., 2011, J Molec Biol 408:177-186), but the mechanisms that control the type of glycosidic linkage still remain unclear. Glucansucrases are often described based on amino acid alignments with other glucansucrase as having an N-terminal variable region, followed by a catalytic domain, and a C-terminal glucan-binding domain (Monchois, et al., 1999, J Bacteriol 181:2290-2292) however, structural analyses of *Lactobacillus reuteri* GTF180-AN and *Streptococcus mutans* GTF-SI show that these glucansucrase proteins that catalyze α(1→6)/α(1→3) linkages actually contain five domains (A, B, C; IV and V) that are formed through a U-shape configuration that involves two regions of the polypeptide for each domain, with the exception of domain C. The amino acid residues of the catalytic triad (aspartate-nucleophile; glutamate-acid/base; aspartate-transition state stabilizer) are located within a deep pocket of domain A, which has a $(\beta/\alpha)_8$ barrel structure (Vujicic-Zagar, id; Ito, id.).

It is thought that the amino acids following the transition state stabilizer determine the orientation of the acceptor molecules and therefore influence the type of glycosidic bond that is formed (Leemhuis et al., 2012, Biocatal Biotransform 30:366-376; Leemhuis et al., 2013, J Biotechnol 163:250-272). The fifth amino acid after the transition stabilizer is likely coupled with the +2 subsite that binds the acceptor molecule and is almost universally an aspartate or threonine among *Streptococcus* and a threonine with *Leuconostoc* species. In streptococci glucansucrase, aspartate is typically associated with insoluble glucan production, while threonine in this position usually results in synthesis of soluble glucan. Substituting D567T in *S. mutans* GtfB shifted production of soluble glucan from 0 to 24%. Conversely, T589D and T598E in GtfD went from 86 to 15% and 86 to 2%, respectively for each mutation (Shimamura, et al., 1994, J Bacteriol 176:4845-4850). Moreover, mutations of this equivalent position in *S. downei* GtfI influenced the structure of the glucan and size of oligosaccharide produced in studies using the catalytic core region in enzymatic assays (Monchois, et al., 2000, Appl Environ Microbiol 66:1923-1927).

Recently identified is a glucansucrase, DsrI, from the type strain of *L. mesenteroides* (NRRL B-1118) that produces a water-insoluble glucan containing approximately 44% α(1→3), 29% α(1→6), 15% terminal non-reducing end residues, and 9% branching through 1,3,6-trisubstituted α-D-glucopyranosyl units (Côté et al., 2012, Appl Microbiol Biotechnol 93:2387-2394). The linkage types apparently occur in discrete sequence domains, with linear segments of α(1→3) linkages interspersed with or grafted onto segments of α(1→6)-linked regions. There is no evidence for an alternan-like structure in the insoluble glucan. This enzyme contains a threonine in position 654 like most other *Leuconostoc* glucansucrases, but its product is unique due to the high percentage of α(1→3) linkages and water-insolubility. Given this property, there is a need to further scrutinize the amino acid at the 654 position to determine whether the catalytic properties of the enzyme and synthesize glucans with different structures can be modified.

BRIEF DESCRIPTION OF THE DRAWINGS

The present invention together with the above and other objects and advantages may best be understood from the following detailed description of the embodiment of the invention illustrated in the drawings, wherein:

FIG. 1 depicts an amino acid alignment of motif IV of GH70 enzymes. Sm GtfB, *S. mutans* GS-5 (GtfB (SEQ ID NO: 4), Accession AAA88588 and GtfD (SEQ ID NO: 7), AAA26895); Ss, *S. salivarius* ATCC 25975 (GtfJ (SEQ ID NO: 5), AAA26896); Sd, *S. downei* MFe28 (GtfI (SEQ ID NO: 6), AAC63063 and GtfS (SEQ ID NO: 8), AAA26898); Lm, *L. mesenteroides* B512F (DsrS (SEQ ID NO: 9), U81374 AAA53749) or NRRL B-1118 (DsrI (SEQ ID NO: 10), YP-_819212). Predominant glycosidic linkage in a-glucan polymer shown in second column; TS, transition stabilizing aspartate; boxed residues, putative amino acid associated with the +2 subsite that binds the acceptor molecule.

(FIG. 7A) T654S. (FIG. 7B) T654I. (FIG. 7C) T654Y. No error bars are included, as this figure is merely intended to show typical shapes of the different types of assay curves.

BRIEF DESCRIPTION OF THE SEQUENCES

Figure 2:
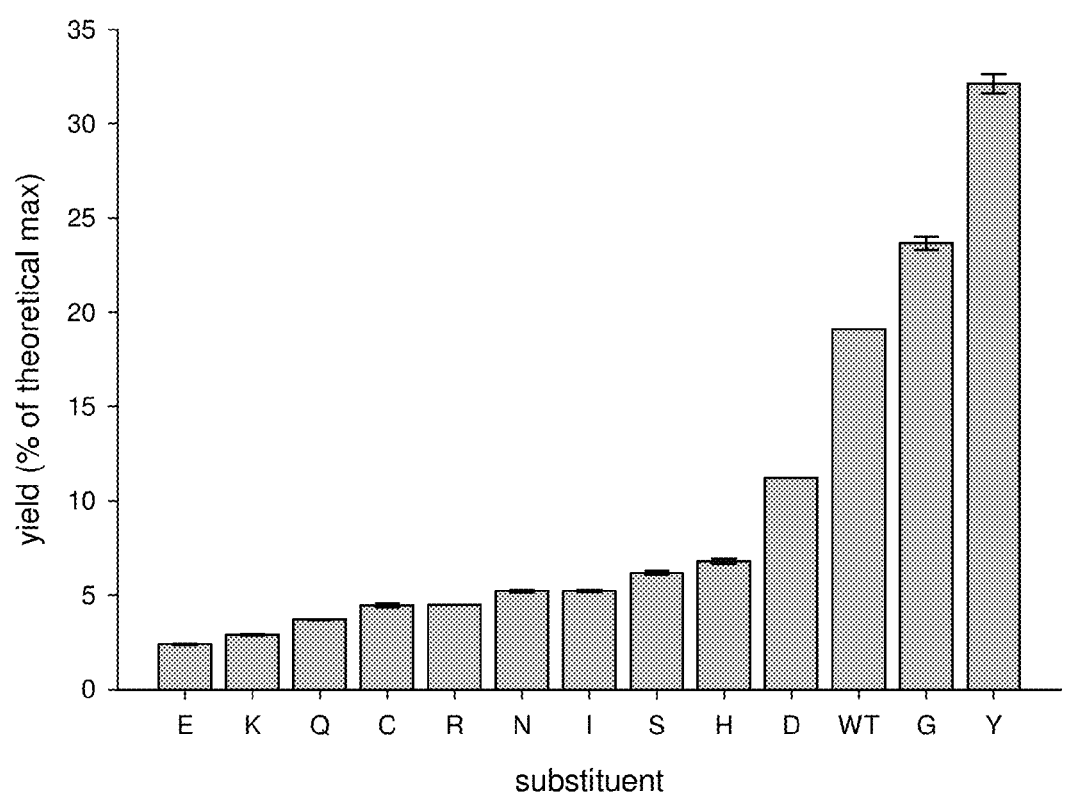
FIG. 2 depict yields of insoluble glucan from each mutant enzyme. Reactions consisted of 2 units glucansucrase (assayed in the absence of dextran) and 2.67 mmoles of sucrose in 8 mL of buffer. Reactions were mixed by rotation and inversion until all sucrose was consumed. Error bars indicate standard error of the mean. Maximum theoretical yield=432 mg.

The invention can be more fully understood from the following detailed description and the accompanying sequence descriptions, which form a part of this application.

SEQ ID NO: 1 is
DVSQNNGVVVATAVDQSNLDATTSDKSITTDDKAATTAATSTDDKATTTV
ATSTDDKDTTTAATSTDDKATTTVATSTDDKATTTAATSTDDKAATTAAT
STDDKAATTAATSTDDKAATTADTSTDDKAATTAATSTDDKATTTAATST
DDKTATTVGTSDNNNSATASDKDVSSSAQKSQTIDNNSKTADTTAALEAS
SKNLKTIDGKTYYYDDDDQVKKNFATVIDGKVLYFDKETGALADTNDYQF
LEGLTSENNTYTEHNASVGTSSDSYTNVDGYLTADSWYRPKDILVNGQNW
ESSKDDDLRPLLMTWWPDKATQVNYLNAMKYLDATETETVYTSDDSQDAL
NKAAQNIQVKIEEKISQEGQTQWLKDDISKFVDSQSNWNIASESKGTDHL
QGGALLYVNSDKTPDANSDYRLLNRTPTNQTGTPLYTTDPTQGGYDFLLA
NDVDNSNPVVQAEQLNWMYYLLNFGSITNNDADANFDSIRVDAVDNVDAD
LLQIAADYFKAAYGVDKSDAISNQHVSILEDWSDNDAEYVKDNGDNQLSM
DNKLRLSLKYSLTMPAVDQYGNKRSGLEPFLTNSLVDRTNDSTDNTAQPN
YSFVRAHDSEVQTVIAEIIKQRIDPDSDGLSPTMDQLTEAFKIYNADQLK
TDKEFTQYNIPSTYATILTNKDTVPRVYYGDMYTDDGQYMATKSLYYDAI
DTLLKSRIKYVSGGQTMSMKYMQGDSSMAADSYRGILTSVRYGNGAMTAT
DAGTNETRTQGIAVIESNNPDLKLSSTDQVVVDMGIAHKNQAYRPALLTT
KDGIDTYVSDSDVSQSLIRYTNSNGQLIFNSSDIVGTANPQVSGYLAVWV
PVGASDTQDARTESSTATTADGQTLHSNAALDSQVIYESFSNFQSTPTTE
AEYANVQIANNTDLYKSWGITNFEFPPQYRSSTDSSFLDSIIQNGYAFTD
RYDLGFNTPTKYGTVDQLRTAIKALHATGIKAMADWVPDQIYNLTGKEVV
AVQRVNNSGIYNQDSVINKTLYASQTVGGGEYQALYGGEFLDEIKKLYPS
LFEKNQISTGVPMDASEKIKEWSAKYFNGTNIQGRGAYYVLKDWATNEYF
KVSTSSNSSVFLPKQLTNEESNTGFISTDGGMTYYSTSGYQAKDTFIQDD
KSNWYYFDKNGYMTYGFQTVNDNNYYFLPNGIELQDAILEDSKGNVYYFN
QYGKQAVDGYYMLANKTWRYFDKNGVMANAGLTTVTVDGQEHIQYFDKNG
IQVKGTSVKDADGKLRYFDTDSGDMVTNRFGENTDGTWSYFGADGIAVTG
AQTISGQKLFFDADGQQIKGKEATDKKGKVHYYDANSGEMITNRFEKLSD
GSWAYFNKKGNIVTGAQVINGQHLFFESNGNQVKGREYTATDGKMRYYDA
DSGDMVTNRFERISDGSWAYFGANGVAVTGEQNINGQQLYFDANGHQVKG
AAVTQADGSQKYYDANSGEMIKS is the amino acid
sequence to wild type glucansucrase.

SEQ ID NO: 2
gcacatgatagtgaagtacaannngttattgctgaaattattaaac
is a primer construct.

SEQ ID NO: 3
gtttaataatttcagcaataacnnnttgtacttcactatcatgtgc
is a primer construct.

Definitions

As used in the specification and claims, the singular form "a", "an" and "the" include plural references unless the context clearly dictates otherwise. For example, the term "a cell" includes a plurality of cells, including mixtures thereof.

As referred to herein, the wild-type ("WT") glucansucrase cloned from *Leuconostoc mesenteroides* NRRL strain B-1118 (ATCC strain 8293).

As described herein, a single amino acid residue substitution can be indicated as follows: the original amino acid residue (expressed as a single-letter abbreviation), followed by the position of the original amino acid residue (i.e., a numerical expression), followed by the new amino acid residue (expressed as a single-letter abbreviation) to be inserted in place of the original amino acid residue. For example, "T654G" means that the original threonine (T) residue at position 654 is to be replaced by the new glycine (G) residue. For multiple substitutions (e.g., double-substitutions, triple-substitutions, and quadruple-substitutions), the various substitutions are separated by either a slash (/) or by a space.

As a practical matter, whether any particular amino acid sequence having at least 96%, 97%, 98% or 99% identical to, for instance, the amino acid sequence described in SEQ. ID. No. X can be determined conventionally using known computer programs to find the best segment of homology between two sequences. When using sequence alignment program to determine whether a particular sequence is, for instance, 96% identical to a reference sequence according to the present invention, the parameters are set, of course, such that the percentage of identity is calculated over the full length of the reference peptide sequence and that gaps in homology of up to 4% of the total number of amino acids in the reference sequence are allowed.

Computer-assisted comparison of SEQ ID NO: 1 with previously reported sequences present in publicly available databases is useful for identifying functional glucansucrase nucleic acid and polypeptide sequences. It will be understood that protein-coding sequences, for example, may be compared as a whole, and that a high degree of sequence homology between two proteins at the amino acid level indicates that the two proteins also possess some degree of functional homology, such as, for example, among enzymes involved in glucansucrase function.

The present invention also relates to a method of recombinantly producing a mutant glucansucrase. This method involves transforming a host cell with at least one heterologous nucleic acid molecule of the present invention under conditions suitable for expression of the modified glucansucrase. The modified glucansucrase is then isolated. Suitable host cells for this method are as described herein (infra).

The present invention further relates to expression vectors wherein a nucleic acid which comprises an expression cassette and which is capable of replicating in a selected host cell or organism. An expression vector may be a plasmid, virus, retrovirus, bacteriophage, cosmid, artificial chromosome (bacterial or yeast), or nucleic acid sequence which is able to replicate in a host cell, characterized by a restriction endonuclease recognition site at which the sequence may be cut in a predetermined fashion for the insertion of a heterologous DNA sequence. An expression vector may include the promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Methods which are well known to those skilled in the art may be used to construct expression vectors containing sequences encoding a glucansucrase and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y, and Ausubel, F. M. et al. (1989) Current Protocols in Molecular Biology, John Wiley & Sons, New York, N.Y.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primers a Laboratory Manual*, Cold Spring Harbor Press, Plainview, N.Y.).

The invention is not limited by the host cell employed.

"Amino acid sequence" as used herein refers to an oligopeptide, peptide, polypeptide, or protein sequence, and fragment thereof, and to naturally occurring or synthetic molecules. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

In the following description, the nomenclature used to define the proteins and peptides is that specified by Schroder and Lubke ["The Peptides," Academic Press (1965)] wherein, in accordance with conventional representation, the N-terminal appears to the left and the C-terminal to the right. Where the amino acid residue has isomeric forms, it is the L-form of the amino acid that is represented herein unless otherwise expressly indicated.

A purified protein or polypeptide of the mutant glucansucrase of the present invention can be obtained by several methods. The purified protein or polypeptide of the modified glucansucrase of the present invention is preferably produced in pure form (preferably at least about 80%, more preferably 90%, pure) by conventional techniques well known in the art. Typically, the purified protein or polypeptide of the glucansucrase of the present invention is secreted into the growth medium of recombinant host cells. Alternatively, the purified protein or polypeptide of the glucansucrase of the present invention is produced but not secreted into growth medium. In such cases, to isolate the protein or polypeptide of the mutant glucansucrase, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the protein or polypeptide of the mutant glucansucrase of the present invention is subjected to gel filtration in an appropriately sized dextran or polyacrylamide column to separate the proteins. If necessary, the protein fraction (containing the mutant phytase of the present invention) may be further purified by HPLC.

As used in the specification and claims, the term "dextranase" refers to an enzyme that catalyzes the endohydrolysis of $\alpha$-(1→6) glucosidic linkages. Typically, commercial dextranase is obtained from extracellular purification of *Penicillium* sp. or *Chaetomium erraticum* cultures.

DETAILED DESCRIPTION OF THE INVENTION

Disclosed herein is a genetically modified enzyme belonging to glycosyltransferases type of glucansucrase comprising at least one mutation at position 654 of said enzyme, wherein modified enzyme is capable to producing a glucan polymer. In one embodiment of the invention, the modified enzyme is derived from *Leuconostoc mesenteroides*. In another embodiment of the invention, the glucan polyer is water-insoluble. In yet another embodiment of the invention the modified enzyme has an amino acid, threonine at position 654, which is replaced with an amino acid selected from the group consisting of glutamic acid, lysine, glutamine, cysteine, arginine, asparagine, isoleucine, serine, histidine, glycine, or aspartic acid, wherein the modified glucansucrase produces a glucan polymer having a higher yield of 1,3-disubstituted α-D-glucopyranosyl units as compared to glucan polymer produced by a wild-type glucansucrase. In yet another embodiment of the invention, the modified enzyme has an amino acid threonine at position 654, which is replaced with tyrosine, wherein the modified glucansucrase produces a glucan polymer having a higher yield of 1,6-disubstituted α-D-glucopyranosyl units as compared to a glucan produced by a wild-type glucansucrase.

FIG. 1 depicts an amino acid alignment of motif IV of several GH70 enzymes. In the figure "Sm GtfB" refers to the motif from *S. mutans* GtfB protein (SEQ ID NO: 4); "Sm GtfD" refers to the motif from *S. mutans* GtfD protein (SEQ ID NO: 7); "Ss GtfJ" refers to the motif from *S. salivarius* GtfJ protein (SEQ ID NO: 5), AAA26896); "Sd Gtf" refers to the motif from *S. downei* GtfI protein (SEQ ID NO: 6); "Sd GtfS" refers to the motif from *S. downei* GtfS protein (SEQ ID NO: 8); "Lm DsrS" refers to the motif from *L. mesenteroides* DsrS protein (SEQ ID NO: 9), and; "Lm DsrI" refers to the motif from *L. mesenteroides* DsrI protein (SEQ ID NO: 10). Predominant glycosidic linkage in α-glucan polymer produced is shown in the second column. "TS" indicates the transition stabilizing aspartate residue. Boxed residues, indicate putative amino acid residues associated with the +2 subsite that binds the acceptor molecule.

Disclosed herein is a glucansucrase comprising the amino acid sequence of SEQ ID NO: 11 with a substitution at position T654, the substitution being either glutamic acid, lysine, glutamine, cysteine, arginine, asparagine, isoleucine, serine, histidine, glycine, or aspartic acid wherein the modified glucansucrase produces a glucan polymer having a higher yield of 1,6-disubstituted .alpha.-D-glucopyranosyl units as compared to a glucan polymer produced by a wild-type glucansucrase.

Also disclosed herein is a glucansucrase comprising the amino acid sequence of SEQ ID NO: 11 with a substitution at position T654, the substitution being tyrosine wherein the modified glucansucrase produces a glucan polymer having a higher yield of 1,3-disubstituted α-D-glucopyranosyl units as compared to a glucan polymer produced by a wild-type glucansucrase.

Also disclosed herein is a method for producing a modified glucansucrase, the steps comprise of producing a modified glucansucrase, wherein the amino acid at position 654 is substituted by a method comprising the steps of: replacing the amino acid at position 654 with glutamic acid, lysine, glutamine, cysteine, arginine, asparagine, isoleucine, serine, histidine, glycine, or aspartic acid, expressing said modified glucansucrase; and using said modified glucansucrase to catalyze the synthesis of a glucan polymer from a carbohydrate source. In another embodiment of the method, the amino acid at position 654 is substituted by a method comprising the steps of: replacing the amino acid at position 654 with tyrosine, expressing said modified glucansucrase; and using said modified glucansucrase to catalyze the synthesis of a glucan polymer from a carbohydrate source.

Also disclosed herein is a modified glycoside hydrolase enzyme comprising at least one mutation to the amino acid downstream from a transition state stabilizer site wherein the modified enzyme produces a glucan polymer. In one embodiment of the invention, the modified enzyme of produces a glucan polymer having a higher yield of 1,3-disubstituted α-D-glucopyranosyl units as compared to a glucan polymer produced by a wild-type glucansucrase. In another embodiment of the invention, the modified enzyme produces a glucan polymer having a higher yield of 1,6-disubstituted α-D-glucopyranosyl units as compared to a glucan polymer produced by a wild-type glucansucrase. In yet another embodiment of the invention, the modified enzyme produces a glucan polymer having a lower water solubility as compared to a glucan polymer produced by a wild-type glucansucrase. In yet another embodiment of the invention, the modified enzyme produces a glucan polymer having a higher water solubility as compared to a glucan polymer produced by a wild-type glucansucrase. In yet another embodiment of the invention, the modified enzyme has a modified amino acid that is the fifth amino acid subsequent to transition state stabilizer.

The equivalent of mature full-length recombinant *L. mesenteroides* DsrI (i.e., only missing secretion signal peptide, which is normally removed during secretion in wt host) was produced using an *E. coli* expression system and purified by immobilized metal ion affinity chromatography as previously described and incorporated by reference herein (Côté et al, 2012, Appl Microbiol Biotechnol 93:2387-2394). Mutations for T654 substitutions in plasmid pSUMO-Dsr403 were introduced using a two-stage PCR protocol followed by DpnI digestion and transformation into *E. coli* (Wang et al., 1999, BioTechniques 26:680-682).

Oligonucleotides used for mutagenesis were Plus Strand 5' gca cat gat agt gaa gta caa nnn gtt att gct gaa att att aaa c 3' (SEQ ID NO. 2) and Minus Strand 5' g ttt aat aat ttc agc aat aac nnn ttg tac ttc act atc atg tgc 3' (SEQ ID NO. 3), whereby nnn is coded for the modified amino acids described below.

Glucansucrase assays and polysaccharide structure determinations were carried out as before (Côté and Skory 2012). Enzyme assays were based on the incorporation of $^{14}$C-labelled glucose from $^{14}$C-(U)-labeled sucrose (PerkinElmer-NEN, Waltham, Mass.) into alcohol-insoluble polysaccharide (i.e., includes water soluble and insoluble fractions), according to a modification of the method described by Germaine et al., 1974, J Dent Res 53:1355-1360). This particular assay measures only glucan synthesis, unlike assays based on release of reducing sugars, which also measure competing reactions such as hydrolysis, leucrose formation, etc. In a typical example, 30 μL of 0.3M $^{14}$C-sucrose in acetate buffer was incubated with 60 μL of enzyme solution at 30° C. At timed intervals, 15 μL aliquots were withdrawn and absorbed onto 1.5 cm squares of Whatman 3MM chromatography/filter paper. The squares were immediately dropped into a beaker containing approximately 150-200 mL of stirred methanol. A metal screen was used to protect the paper squares from maceration by the stir bar. After washing with three changes of methanol for ten minutes per wash, they were dried under a heat lamp and counted for $^{14}$C content in Ecolume cocktails (MPBio, Solon, Ohio) using a Beckman-Coulter (Brea, Calif.) LSC-6500 liquid scintillation counter. An enzyme unit is defined here as the amount of enzyme activity that incorporates one μmole of glucose into glucan in one minute.

For product analysis, enzyme was incubated with 0.3 M sucrose and the reaction was monitored by thin-layer chromatography as previously described in Côté et al., 1982, Carbohydr Res 111:127-142 and incorporated by reference herein.

After all of the sucrose had been consumed, the insoluble product was collected, washed to remove remaining sugars and oligosaccharides, dried for mass yield determination, and analyzed by a combination of methylation analysis, $^{13}$C-NMR spectroscopy, and measurement of solubilization by endodextranase as previously described (Côté, 2012, Appl Microbiol Biotechnol 93:2387-2394). Water-insoluble glucans were soluble in either dimethyl sulfoxide-water mixtures (DMSO:H$_2$O 9:1, vol) or 1M NaOH (aq.) (Lamberts et al., 1975, J Dent Res 54:857-866). 1M NaOH (aq.) with deuterated NaOD in D$_2$O was selected for NMR analyses because most previous studies on streptococcal glucans have been done in that system. Yields of insoluble glucan from each mutant enzyme were determined under identical conditions for each mutant: reactions consisted of 2 units glucansucrase (assayed in the absence of dextran) and 2.67 mmoles of sucrose in 8 mL of buffer. Insoluble glucan was recovered by centrifugation, followed by three washes with 8 mL water, one wash in 50% ethanol, and one wash in absolute ethanol, followed by drying in vacuo at 50° C.

EXAMPLE 1

Product Formation

The yields of insoluble glucan produced by each mutant enzyme varied significantly, with most of the modified enzymes producing less insoluble glucan than the wild type enzyme under the tested conditions (FIG. 2). However, two modifications, T654G and T654Y, resulted in enzymes that produced more insoluble glucan than the wild type. The remaining mutants, with the exception of T654D, produced less than half of the amount obtained with the wild type enzyme. All of the yields were less than half of the theoretical yield, 432 mg, from sucrose, despite the fact that all of the sucrose was consumed. The remainder of the sucrose appeared to be diverted to the production of leucrose, palatinose and higher oligosaccharides, as large amounts of these products were observed on TLC. The higher oligosaccharides presumably arise from glucosylation of leucrose and palatinose, as they were chromatographically similar to those products from alternansucrase acceptor reactions with fructose (Côté et al., 2008, Biocatal Biotransform 26:161-168).

Interestingly, the six highest yields, with the exception of T654D, had amino acids in position 654 that are defined as neutral hydropathy (i.e., hydropathy index −0.4 to −3.2) according to the Kyte-Doolittle scale (Kyte & Doolittle, 1982, J Molec Biol 157:105-132). There did not appear to be any correlation between yield and charge, polarity, or amino acid size (e.g., molecular weight and volume). In fact, the two highest yields were obtained with the largest (Y; MW 181.2 Da) and smallest (G; MW 75.1 Da) amino acid substitutions.

α-Glucan Structure and Properties

Figure 3:
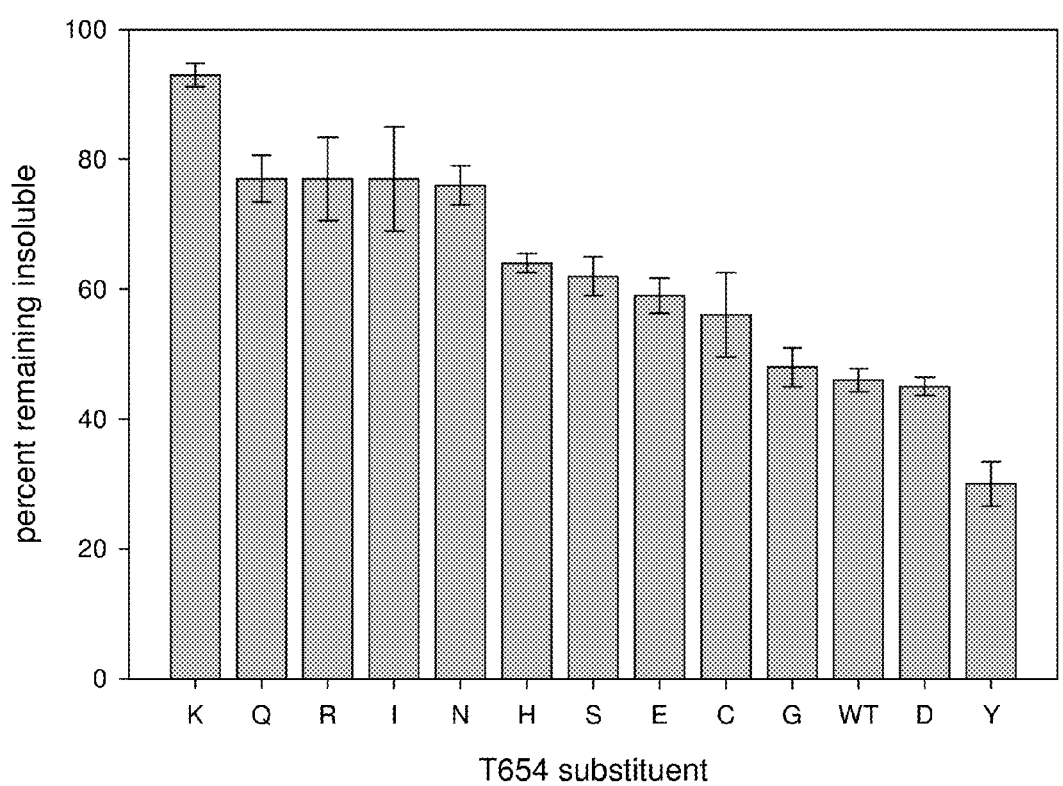
FIG. 3 depicts endodextranase resistance of insoluble glucans produced by DSR-I from T654 substitution mutants. Bars represent relative amount of glucan remaining water-insoluble after treatment with *Chaetomium* sp. endodextranase. Error bars represent standard error of the mean.
Figure 4:
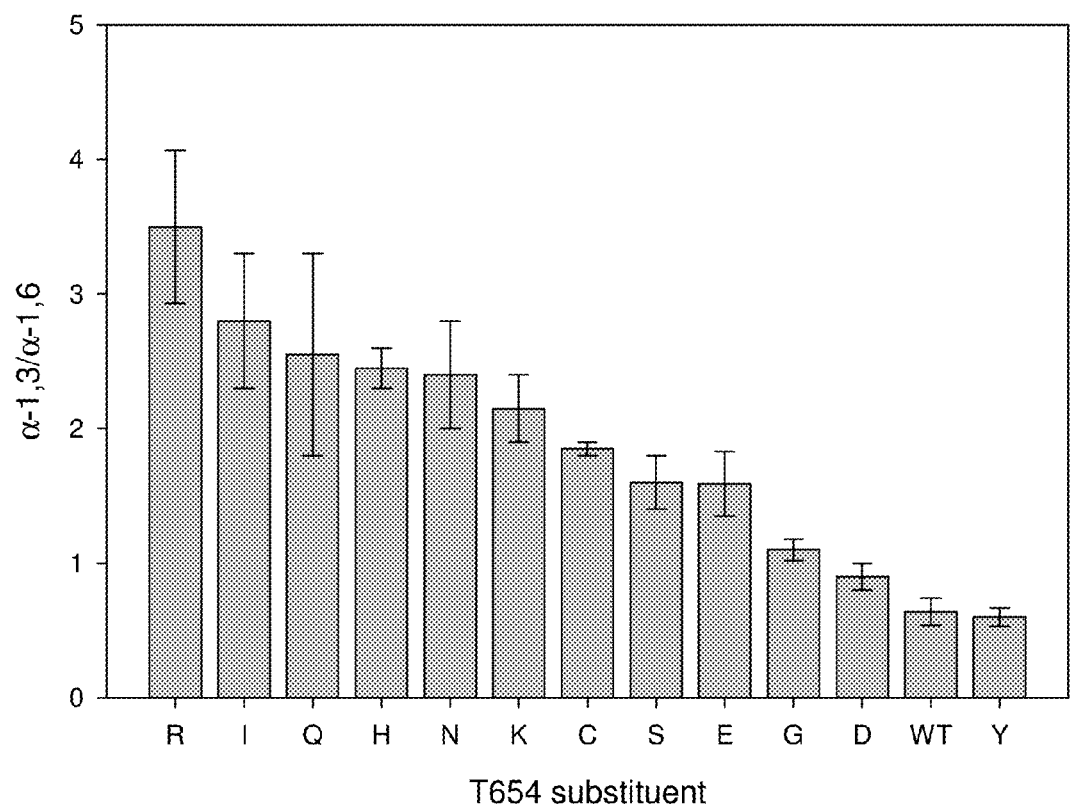
FIG. 4 depicts anomeric peak height ratio of insoluble glucans produced by DSR-I from T654 substitution mutants. Ratios were calculated from height of $^{13}$C-NMR peaks representing carbon-1 in an ∀-(1→3) linkage (101.6 ppM) divided by peak height of carbon-1 in an ∀-(1→6) linkage (98.7 ppM). Error bars represent standard error of the mean.
Figure 5:
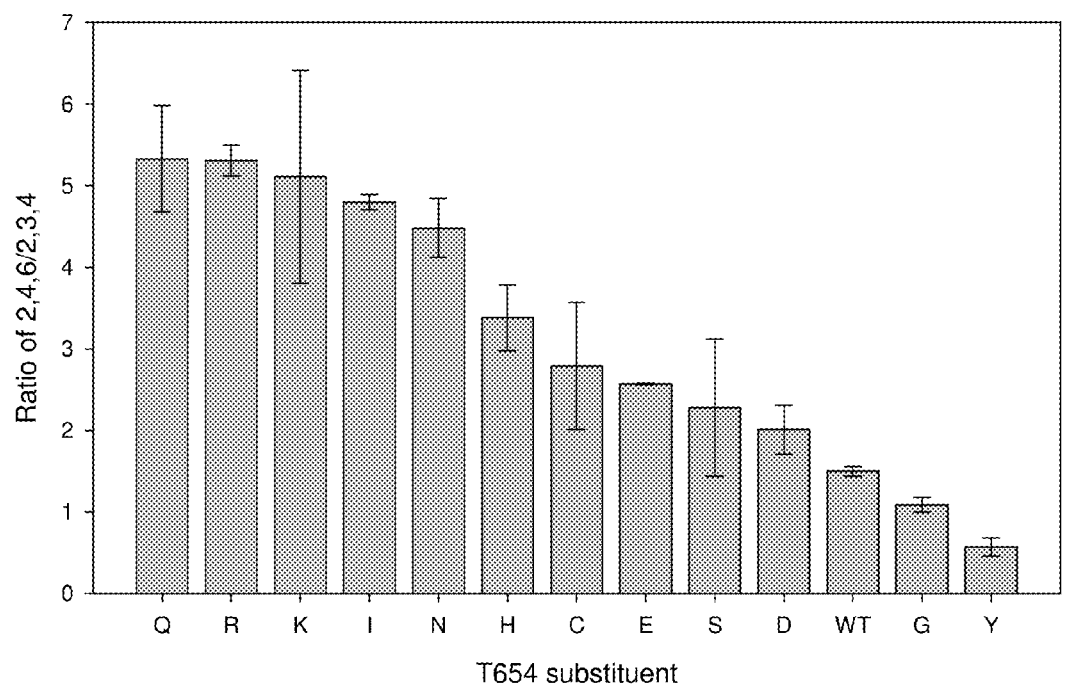
FIG. 5 depicts graph from a methylation analysis for the ratio of 3-mono-O-substituted glucopyranosyl units to 6-mono-O-substituted glucopyranosyl units in insoluble glucans produced by DSR-I from T654 substitution mutants. Ratio was calculated by dividing molar proportion of 2,4,6-tri-O-methyl glucose derivative by molar proportion of 2,3,4-tri-O-methyl glucose derivative obtained in methylation analyses. Error bars represent standard error of the mean.

The three methods used to measure the amount of 1,3-disubstituted α-D-glucopyranosyl units in the insoluble glucans were generally in agreement, although some small differences can be seen when comparing FIGS. 3, 4, and 5. When all three methods of measurement are taken together, the mutants may be divided into three groups. Those producing insoluble glucans with the highest proportion of 1,3-disubstituted α-D-glucopyranosyl units (α(1→3)/α(1→6) ratio>2) included Q, R, I, N, K, and H. The second group comprises those producing glucans with a α(1→3)/α(1→6) ratio<2 and includes C, S, G, E, D, and WT. The third group produced glucan with significantly lower α(1→3)/α(1→6) ratio and greater endodextranase susceptibility compared to WT and contains only one mutant, Y.

Contrary to the trends regarding yield and amino acid hydropathy, the highest percentage of α(1→3) linkages were associated with the most hydrophilic (Q, N, R, K, H; in order of hydrophilicity) and hydrophobic (I) residues. The exception was with the acidic residues D and E. The percentage of α(1→3) linkages for D was approximately the same as WT in all of the studies, but the α-glucan from E was significantly higher as indicated by NMR and endodextranase treatment. Glucan from these two acidic residues along with the most neutral amino acids (C, S, G, T, H, and Y) had the lowest percentage of α(1→3) linkages of all of those tested. The largest residue, Y, by both MW (181.2 Da) and volume 194 Å$^3$ produced glucan with the lowest percentage of α(1→3) linkages; however, the other aromatic residue, H, actually produced glucan with significantly more α(1→3) linkages.

The insoluble glucans produced by each mutant enzyme differed in appearance. Although some of the observed differences may be due to differing amounts and concentrations of glucan formed, some properties were consistently noted regardless of concentration. The glucans with lower levels of α(1→3) linkages, namely those from T654 Y, WT, G and D, were gel-like and adhered to the glass surfaces, whereas those with higher levels of α(1→3) linkages, namely T654 K, R, N, Q and I, were dispersed as fine particles, and did not adhere as strongly to the glass.

No general conclusion can be drawn regarding the type of amino acid substitution that will lead to lower levels of 1,3-disubstituted α-D-glucopyranosyl units, since only one example (tyrosine) was found. Furthermore, none of the tested amino acid substitutions yielded an enzyme with significantly higher specific activity.

Figure 6:
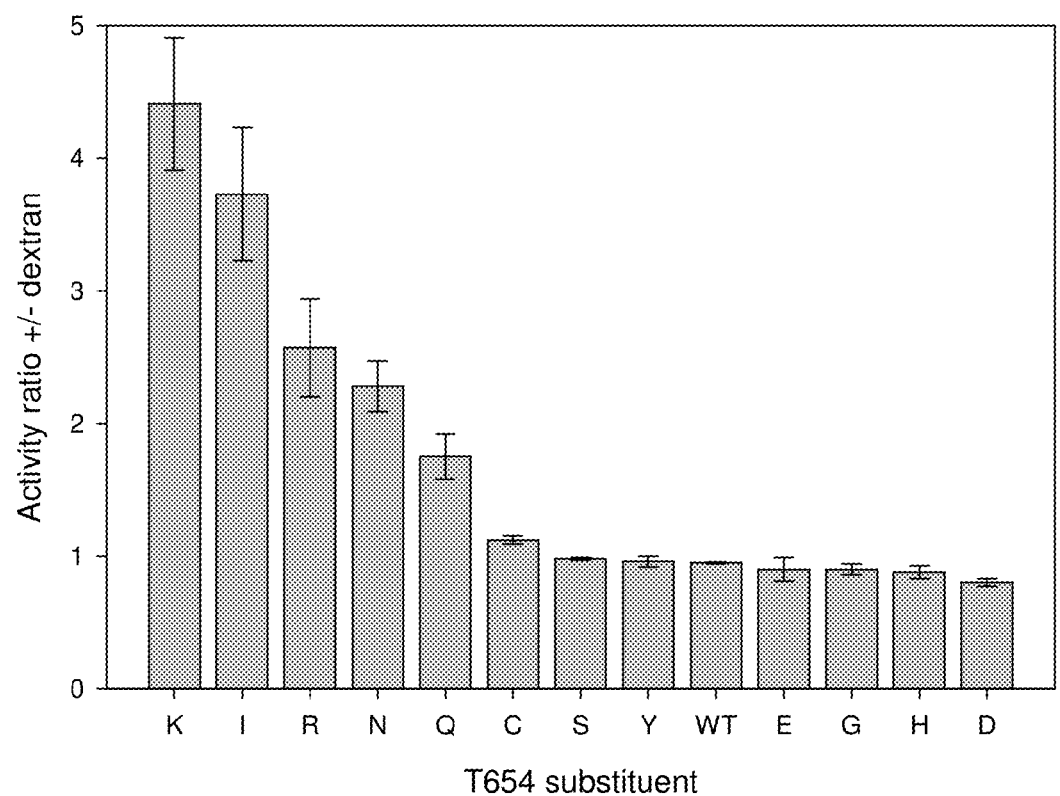
FIG. 6 depicts a graph for the activation or lack thereof by the addition of soluble dextran to radioassay mixtures. Mixtures contained 50 μL of enzyme solution, 50 μL of 0.3M $^{14}$C-U-sucrose, and 50 μL of either 2% (w/v) commercial dextran (Mw=2,000,000) or buffer. Error bars indicate standard errors of the mean ratios.
Figure 7A:
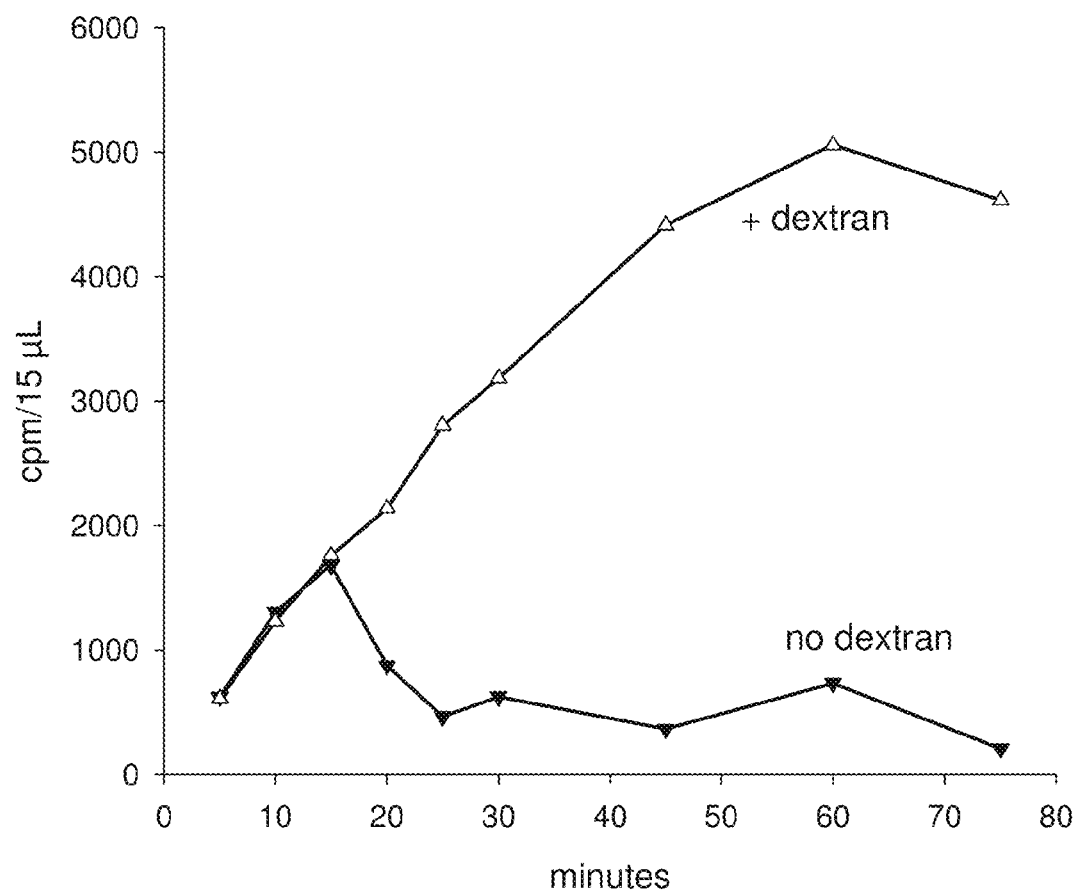
FIGS. 7A-C depict graphs of representative examples of radioassays of mutant enzymes in the absence or presence of dextran. Assays consisted of 50 μL of enzyme solution, 50 μL of 0.3M $^{14}$C-U-sucrose (52 cpm/μg), and 50 μL of either 2% (w/v) commercial dextran (Mw=2,000,000) or buffer. At indicated time points, 15 μL aliquots were analyzed for methanol-insoluble $^{14}$C-glucan.

When the mutant enzymes were assayed in the absence and presence of dextran, two different phenomena were observed. Some of the enzymes exhibited an increase in initial rate of glucan synthesis in the presence of added dextran, whereas others showed no such effect. FIG. 6 shows that mutants substituted at position 654 with I, K, R, N and Q were activated by dextran, but none of the other mutants were significantly affected. FIG. 7 shows three typical radioassay plots. In FIG. 7A, mutant T654S shows no effect of dextran on the initial rate. After approximately 15 minutes, small particles of gel were seen forming in the reaction mixture. These insoluble particles were not pipetted onto the filter paper squares, and thus not counted as newly synthesized $^{14}$C-glucan. This gives rise to a great deal of scatter and inconsistency in the assay plot. However, when dextran was present, no such particles were seen, and the solution remained uniform, thus enabling the consistent counting of increasing amounts of $^{14}$C-glucan product. A similar effect on product solubility was noted with mutant T654I, but in that case (as well as T654 mutants K, Q, R and N), the initial rate was significantly higher when dextran was present. Finally, with mutant T654Y, no activation was observed, and the product remained relatively soluble throughout the course of the reaction regardless of the presence or absence of dextran. The molecular weight of the dextran added apparently made no difference. With mutant T654I, for example, the assay curves were identical with dextrans of 2,000 kDa, 20 kDa, 10 kDa and 6 kDa.

The majority of the T654 substitutions yielded glucansucrase that produced an insoluble glucan with a percentage of 1,3-disubstituted α-D-glucopyranosyl units equal to or greater than the wild type enzyme (FIGS. 3, 4, 5); however, this was often at the expense of yield (FIG. 2) or specific activity. In general, most of the modified enzymes exhibited lower specific activity than the wild type. The only exception was tyrosine, which produced an enzyme whose product contains fewer 1,3-disubstituted α-D-glucopyranosyl units, but had a higher yield than the WT enzyme. Modified enzymes producing glucans with the highest amount of 1,3-disubstituted α-D-glucopyranosyl units included all of those with nitrogen in the side chains (Q, R, N, K). Histidine may also be included in this group, although the effect was less clear. It may be that the effect of the nitrogen in histidine was offset by the effect of the aromatic ring structure, rendering it similar to tyrosine in that regard. Modifications in which threonine 654 was substituted with acidic amino acids (D, E), alcohols or thiols (S or C) as well as G, seemed to be the most similar to the wild type in terms of 1,3-disubstituted α-D-glucopyranosyl units in their product glucans. In most cases, these latter enzymes also exhibited slightly higher specific activities, perhaps another indication of their greater similarity to the wild type enzyme.

EXAMPLE 2

Activation by Dextran

Figure 7B:
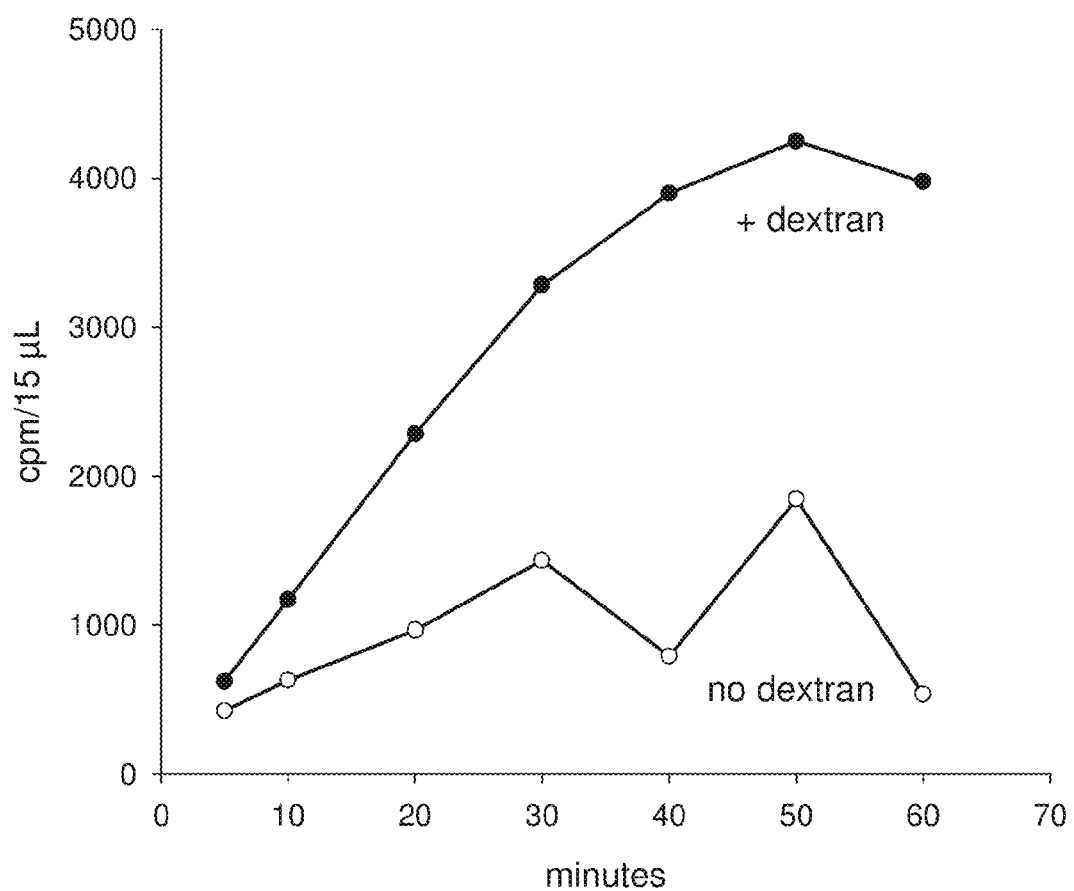
Figure 7C:
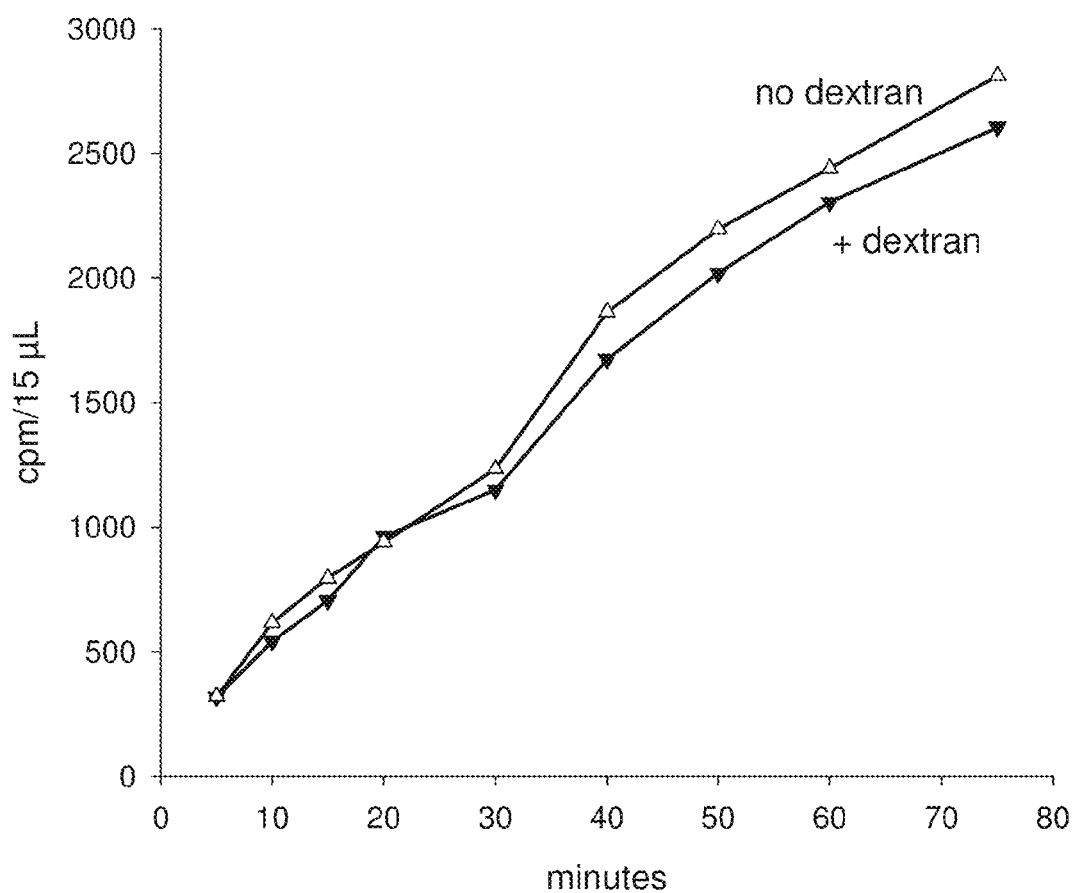

The addition of dextran to the radioassay solutions could markedly increase the initial rate of synthesis by some of the modified enzymes (FIG. 6). The molecular weight of various commercial (NRRL B-512F) dextrans seemed to have little effect on the degree of activation. Mutated enzymes that produced higher levels of α(1→3) linkages showed the greatest increase in activity, up to 5-fold for T654K. It was also noted that the addition of dextran to assay reactions of some of the mutants was effective in preventing or delaying the formation of insoluble product, resulting in linear assay curves for a longer period of time (FIG. 7). Enzymes that were not activated by dextran had overlapping curves (FIGS. 7A and 7C) until the solubility of the glucan was presumably exceeded. However, enzymes that were activated by dextran had distinctly different initial rate slopes (FIG. 7B). Other homopolysaccharides were also analyzed for their ability to similarly activate the mutant DSR-I enzymes. Soluble starch and pullulan had no measurable effect. Highly branched NRRL B-742 fraction S dextran (Côté & Robyt, 1983, Carbohydr Res 119: 141-156) and alternan from several NRRL strains activated the DSR-I from mutants K, R, N, Q and I nearly as well as did dextran. Upon information and belief, any glucan having unbranched sequences of α(1→6) linkages would activate the glucansucrase disclosed herein.

The effects of dextran addition are due to two different causes. The activation of initial rates appears to be an allosteric effect whereby the efficiency of glucan synthesis is improved by binding of dextran to the glucan-binding domain, although earlier researchers did not differentiate between such allosteric activation and a so-called "primer effect" of dextran on streptococcal glucansucrases (e.g., Germaine et al., 1977, Infect Immun 16:637-648; Fukushima et al., 1981, J Dent Res 60:1707-1712; Sato et al, 1982, Microbios 34:99-112; Hanada et al, 1986, FEMS Microbiol Lett 36:173-175). The solubility effect may be due to the formation of graft copolymers, whereby the dextran acts as an acceptor for the transfer of glucosyl and/or glucanosyl units to the dextran chain. This conclusion is based on previous reports that GTF-I from *Streptococcus* spp. carries out similar reactions.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto."

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. A modified glucansucrase enzyme comprising an amino acid sequence that is at least 96% identical to SEQ ID NO:11, wherein the threonine residue at position 654 is substituted with glutamic acid, lysine, glutamine, cysteine, arginine, asparagine, isoleucine, serine, histidine, glycine, or aspartic acid, and wherein the modified enzyme is capable of producing a glucan polymer.

2. The modified enzyme of claim 1, wherein the enzyme is obtained from *Leuconostoc* mesenteroides.

3. The modified enzyme of claim 1, wherein the glucan polymer is water-insoluble.

4. The modified enzyme of claim 1, wherein the threonine is replaced with tyrosine, and wherein the modified enzyme produces a glucan polymer having a higher yield of 1,6-disubstituted α-D-glucopyranosyl units as compared to a glucan produced by a wild-type glucansucrase.

5. The modified enzyme of claim 4, wherein the wild-type glucansucrase is from *Leuconostoc* mesenteroides NRRL B-1118.

6. The modified enzyme of claim 5, wherein the modified glucansucrase produces a glucan polymer that is more water insoluble as compared to a glucan polymer produced by a glucansucrase produced by *Leuconostoc* mesenteroides NRRL B-1118.

7. The modified glucansucrase of claim 1, wherein the threonine residue is substituted with tyrosine, and wherein the modified glucansucrase produces a glucan polymer having a higher yield of 1,3-disubstituted α-D-glucopyranosyl units as compared to a glucan polymer produced by a wild-type glucansucrase.

8. The modified enzyme of claim 7, wherein the wild-type glucansucrase is from *Leuconostoc* mesenteroides NRRL B-1118.

9. A method for producing a glucan polymer with a modified glucansucrase, comprising the steps of expressing the modified glucansucrase of claim 1 in a recombinant host cell, and; using the modified glucansucrase to catalyze the synthesis of a glucan polymer from a carbohydrate source, thus producing the glucan polymer.

10. A method for producing a glucan polymer with a modified glucansucrase, comprising the steps of expressing the modified glucansucrase of claim 7 in a recombinant host cell, and; using the modified glucansucrase to catalyze the synthesis of a glucan polymer from a carbohydrate source, thus producing the glucan polymer.

11. A method for producing a water-insoluble gel wherein a glucan polymer is formed by the modified enzyme of claim 1, and a carbohydrate source.

\* \* \* \* \*

SEQUENCE LISTING

```
<160> NUMBER OF SEQ ID NOS: 11

<210> SEQ ID NO 1
<211> LENGTH: 1473
<212> TYPE: PRT
<213> ORGANISM: glucansucrase

<400> SEQUENCE: 1

Asp Val Ser Gln Asn Asn Gly Val Val Ala Thr Ala Val Asp Gln
1               5                   10                  15

Ser Asn Leu Asp Ala Thr Thr Ser Asp Lys Ser Ile Thr Thr Asp Asp
                20                  25                  30

Lys Ala Ala Thr Thr Ala Ala Thr Ser Thr Asp Asp Lys Ala Thr Thr
            35                  40                  45

Thr Val Ala Thr Ser Thr Asp Asp Lys Asp Thr Thr Thr Ala Ala Thr
        50                  55                  60

Ser Thr Asp Asp Lys Ala Thr Thr Thr Val Ala Thr Ser Thr Asp Asp
65                  70                  75                  80
```

```
Lys Ala Thr Thr Thr Ala Ala Thr Ser Thr Asp Asp Lys Ala Ala Thr
                85                  90                  95

Thr Ala Ala Thr Ser Thr Asp Asp Lys Ala Ala Thr Ala Ala Thr
            100                 105                 110

Ser Thr Asp Asp Lys Ala Ala Thr Thr Ala Asp Thr Ser Thr Asp Asp
            115                 120                 125

Lys Ala Ala Thr Thr Ala Ala Thr Ser Thr Asp Asp Lys Ala Thr Thr
            130                 135                 140

Thr Ala Ala Thr Ser Thr Asp Asp Lys Thr Ala Thr Thr Val Gly Thr
145                 150                 155                 160

Ser Asp Asn Asn Asn Ser Ala Thr Ala Ser Asp Lys Asp Val Ser Ser
                165                 170                 175

Ser Ala Gln Lys Ser Gln Thr Ile Asp Asn Asn Ser Lys Thr Ala Asp
            180                 185                 190

Thr Thr Ala Ala Leu Glu Ala Ser Ser Lys Asn Leu Lys Thr Ile Asp
            195                 200                 205

Gly Lys Thr Tyr Tyr Tyr Asp Asp Asp Gln Val Lys Lys Asn Phe
        210                 215                 220

Ala Thr Val Ile Asp Gly Lys Val Leu Tyr Phe Asp Lys Glu Thr Gly
225                 230                 235                 240

Ala Leu Ala Asp Thr Asn Asp Tyr Gln Phe Leu Glu Gly Leu Thr Ser
                245                 250                 255

Glu Asn Asn Thr Tyr Thr Glu His Asn Ala Ser Val Gly Thr Ser Ser
            260                 265                 270

Asp Ser Tyr Thr Asn Val Asp Gly Tyr Leu Thr Ala Asp Ser Trp Tyr
            275                 280                 285

Arg Pro Lys Asp Ile Leu Val Asn Gly Gln Asn Trp Glu Ser Ser Lys
290                 295                 300

Asp Asp Asp Leu Arg Pro Leu Leu Met Thr Trp Trp Pro Asp Lys Ala
305                 310                 315                 320

Thr Gln Val Asn Tyr Leu Asn Ala Met Lys Tyr Leu Asp Ala Thr Glu
            325                 330                 335

Thr Glu Thr Val Tyr Thr Ser Asp Asp Ser Gln Asp Ala Leu Asn Lys
            340                 345                 350

Ala Ala Gln Asn Ile Gln Val Lys Ile Glu Glu Lys Ile Ser Gln Glu
            355                 360                 365

Gly Gln Thr Gln Trp Leu Lys Asp Asp Ile Ser Lys Phe Val Asp Ser
        370                 375                 380

Gln Ser Asn Trp Asn Ile Ala Ser Glu Ser Lys Gly Thr Asp His Leu
385                 390                 395                 400

Gln Gly Gly Ala Leu Leu Tyr Val Asn Ser Asp Lys Thr Pro Asp Ala
                405                 410                 415

Asn Ser Asp Tyr Arg Leu Leu Asn Arg Thr Pro Thr Asn Gln Thr Gly
            420                 425                 430

Thr Pro Leu Tyr Thr Thr Asp Pro Thr Gln Gly Gly Tyr Asp Phe Leu
            435                 440                 445

Leu Ala Asn Asp Val Asp Asn Ser Asn Pro Val Val Gln Ala Glu Gln
450                 455                 460

Leu Asn Trp Met Tyr Tyr Leu Leu Asn Phe Gly Ser Ile Thr Asn Asn
465                 470                 475                 480

Asp Ala Asp Ala Asn Phe Asp Ser Ile Arg Val Asp Ala Val Asp Asn
                485                 490                 495
```

```
Val Asp Ala Asp Leu Leu Gln Ile Ala Ala Asp Tyr Phe Lys Ala Ala
            500                 505                 510

Tyr Gly Val Asp Lys Ser Asp Ala Ile Ser Asn Gln His Val Ser Ile
        515                 520                 525

Leu Glu Asp Trp Ser Asp Asn Asp Ala Glu Tyr Val Lys Asp Asn Gly
    530                 535                 540

Asp Asn Gln Leu Ser Met Asp Asn Lys Leu Arg Leu Ser Leu Lys Tyr
545                 550                 555                 560

Ser Leu Thr Met Pro Ala Val Asp Gln Tyr Gly Asn Lys Arg Ser Gly
                565                 570                 575

Leu Glu Pro Phe Leu Thr Asn Ser Leu Val Asp Arg Thr Asn Asp Ser
            580                 585                 590

Thr Asp Asn Thr Ala Gln Pro Asn Tyr Ser Phe Val Arg Ala His Asp
        595                 600                 605

Ser Glu Val Gln Thr Val Ile Ala Glu Ile Ile Lys Gln Arg Ile Asp
    610                 615                 620

Pro Asp Ser Asp Gly Leu Ser Pro Thr Met Asp Gln Leu Thr Glu Ala
625                 630                 635                 640

Phe Lys Ile Tyr Asn Ala Asp Gln Leu Lys Thr Asp Lys Glu Phe Thr
                645                 650                 655

Gln Tyr Asn Ile Pro Ser Thr Tyr Ala Thr Ile Leu Thr Asn Lys Asp
            660                 665                 670

Thr Val Pro Arg Val Tyr Tyr Gly Asp Met Tyr Thr Asp Asp Gly Gln
        675                 680                 685

Tyr Met Ala Thr Lys Ser Leu Tyr Tyr Asp Ala Ile Asp Thr Leu Leu
    690                 695                 700

Lys Ser Arg Ile Lys Tyr Val Ser Gly Gly Gln Thr Met Ser Met Lys
705                 710                 715                 720

Tyr Met Gln Gly Asp Ser Ser Met Ala Ala Asp Ser Tyr Arg Gly Ile
                725                 730                 735

Leu Thr Ser Val Arg Tyr Gly Asn Gly Ala Met Thr Ala Thr Asp Ala
            740                 745                 750

Gly Thr Asn Glu Thr Arg Thr Gln Gly Ile Ala Val Ile Glu Ser Asn
        755                 760                 765

Asn Pro Asp Leu Lys Leu Ser Ser Thr Asp Gln Val Val Asp Met
    770                 775                 780

Gly Ile Ala His Lys Asn Gln Ala Tyr Arg Pro Ala Leu Leu Thr Thr
785                 790                 795                 800

Lys Asp Gly Ile Asp Thr Tyr Val Ser Asp Ser Asp Val Ser Gln Ser
                805                 810                 815

Leu Ile Arg Tyr Thr Asn Ser Asn Gly Gln Leu Ile Phe Asn Ser Ser
            820                 825                 830

Asp Ile Val Gly Thr Ala Asn Pro Gln Val Ser Gly Tyr Leu Ala Val
        835                 840                 845

Trp Val Pro Val Gly Ala Ser Asp Thr Gln Asp Ala Arg Thr Glu Ser
    850                 855                 860

Ser Thr Ala Thr Thr Ala Asp Gly Gln Thr Leu His Ser Asn Ala Ala
865                 870                 875                 880

Leu Asp Ser Gln Val Ile Tyr Glu Ser Phe Ser Asn Phe Gln Ser Thr
                885                 890                 895

Pro Thr Thr Glu Ala Glu Tyr Ala Asn Val Gln Ile Ala Asn Asn Thr
            900                 905                 910

Asp Leu Tyr Lys Ser Trp Gly Ile Thr Asn Phe Glu Phe Pro Pro Gln
```

-continued

```
            915                 920                 925
Tyr Arg Ser Ser Thr Asp Ser Ser Phe Leu Asp Ser Ile Ile Gln Asn
            930                 935                 940

Gly Tyr Ala Phe Thr Asp Arg Tyr Asp Leu Gly Phe Asn Thr Pro Thr
945                 950                 955                 960

Lys Tyr Gly Thr Val Asp Gln Leu Arg Thr Ala Ile Lys Ala Leu His
                965                 970                 975

Ala Thr Gly Ile Lys Ala Met Ala Asp Trp Val Pro Asp Gln Ile Tyr
                980                 985                 990

Asn Leu Thr Gly Lys Glu Val Val  Ala Val Gln Arg Val  Asn Asn Ser
                995                 1000                1005

Gly Ile  Tyr Asn Gln Asp Ser  Val Ile Asn Lys Thr  Leu Tyr Ala
        1010                1015                1020

Ser Gln  Thr Val Gly Gly  Glu Tyr Gln Ala Leu  Tyr Gly Gly
        1025                1030                1035

Glu Phe  Leu Asp Glu Ile Lys  Lys Leu Tyr Pro Ser  Leu Phe Glu
        1040                1045                1050

Lys Asn  Gln Ile Ser Thr Gly  Val Pro Met Asp Ala  Ser Glu Lys
        1055                1060                1065

Ile Lys  Glu Trp Ser Ala Lys  Tyr Phe Asn Gly Thr  Asn Ile Gln
        1070                1075                1080

Gly Arg  Gly Ala Tyr Tyr Val  Leu Lys Asp Trp Ala  Thr Asn Glu
        1085                1090                1095

Tyr Phe  Lys Val Ser Thr Ser  Ser Asn Ser Ser Val  Phe Leu Pro
        1100                1105                1110

Lys Gln  Leu Thr Asn Glu Glu  Ser Asn Thr Gly Phe  Ile Ser Thr
        1115                1120                1125

Asp Gly  Gly Met Thr Tyr Tyr  Ser Thr Ser Gly Tyr  Gln Ala Lys
        1130                1135                1140

Asp Thr  Phe Ile Gln Asp Asp  Lys Ser Asn Trp Tyr  Tyr Phe Asp
        1145                1150                1155

Lys Asn  Gly Tyr Met Thr Tyr  Gly Phe Gln Thr Val  Asn Asp Asn
        1160                1165                1170

Asn Tyr  Tyr Phe Leu Pro Asn  Gly Ile Glu Leu Gln  Asp Ala Ile
        1175                1180                1185

Leu Glu  Asp Ser Lys Gly Asn  Val Tyr Tyr Phe Asn  Gln Tyr Gly
        1190                1195                1200

Lys Gln  Ala Val Asp Gly Tyr  Tyr Met Leu Ala Asn  Lys Thr Trp
        1205                1210                1215

Arg Tyr  Phe Asp Lys Asn Gly  Val Met Ala Asn Ala  Gly Leu Thr
        1220                1225                1230

Thr Val  Thr Val Asp Gly Gln  Glu His Ile Gln Tyr  Phe Asp Lys
        1235                1240                1245

Asn Gly  Ile Gln Val Lys Gly  Thr Ser Val Lys Asp  Ala Asp Gly
        1250                1255                1260

Lys Leu  Arg Tyr Phe Asp Thr  Asp Ser Gly Asp Met  Val Thr Asn
        1265                1270                1275

Arg Phe  Gly Glu Asn Thr Asp  Gly Thr Trp Ser Tyr  Phe Gly Ala
        1280                1285                1290

Asp Gly  Ile Ala Val Thr Gly  Ala Gln Thr Ile Ser  Gly Gln Lys
        1295                1300                1305

Leu Phe  Phe Asp Ala Asp Gly  Gln Gln Ile Lys Gly  Lys Glu Ala
        1310                1315                1320
```

```
Thr Asp Lys Lys Gly Lys Val His Tyr Tyr Asp Ala Asn Ser Gly
    1325                1330                1335

Glu Met Ile Thr Asn Arg Phe Glu Lys Leu Ser Asp Gly Ser Trp
    1340                1345                1350

Ala Tyr Phe Asn Lys Lys Gly Asn Ile Val Thr Gly Ala Gln Val
    1355                1360                1365

Ile Asn Gly Gln His Leu Phe Phe Glu Ser Asn Gly Asn Gln Val
    1370                1375                1380

Lys Gly Arg Glu Tyr Thr Ala Thr Asp Gly Lys Met Arg Tyr Tyr
    1385                1390                1395

Asp Ala Asp Ser Gly Asp Met Val Thr Asn Arg Phe Glu Arg Ile
    1400                1405                1410

Ser Asp Gly Ser Trp Ala Tyr Phe Gly Ala Asn Gly Val Ala Val
    1415                1420                1425

Thr Gly Glu Gln Asn Ile Asn Gly Gln Gln Leu Tyr Phe Asp Ala
    1430                1435                1440

Asn Gly His Gln Val Lys Gly Ala Ala Val Thr Gln Ala Asp Gly
    1445                1450                1455

Ser Gln Lys Tyr Tyr Asp Ala Asn Ser Gly Glu Met Ile Lys Ser
    1460                1465                1470

<210> SEQ ID NO 2
<211> LENGTH: 46
<212> TYPE: DNA
<213> ORGANISM: ARTIFICIAL SEQUENCE
<220> FEATURE:
<223> OTHER INFORMATION: CHEMICALLY SYTHESIZED
<220> FEATURE:
<221> NAME/KEY: misc_feature
<222> LOCATION: (22)..(24)
<223> OTHER INFORMATION: n is a, c, g, or t

<400> SEQUENCE: 2
gcacatgata gtgaagtaca anngttatt gctgaaatta ttaaac          46

<210> SEQ ID NO 3
<211> LENGTH: 46
<212> TYPE: DNA
<213> ORGANISM: ARTIFICIAL SEQUENCE
<220> FEATURE:
<223> OTHER INFORMATION: CHEMICALLY SYNTHESIZED
<220> FEATURE:
<221> NAME/KEY: misc_feature
<222> LOCATION: (23)..(25)
<223> OTHER INFORMATION: n is a, c, g, or t

<400> SEQUENCE: 3
gtttaataat ttcagcaata acnnnttgta cttcactatc atgtgc          46

<210> SEQ ID NO 4
<211> LENGTH: 21
<212> TYPE: PRT
<213> ORGANISM: Streptococcus mutans

<400> SEQUENCE: 4

Phe Ile Arg Ala His Asp Ser Glu Val Gln Asp Leu Ile Ala Asp Ile
1               5                   10                  15

Ile Lys Ala Glu Ile
            20

<210> SEQ ID NO 5
```

-continued

```
<211> LENGTH: 21
<212> TYPE: PRT
<213> ORGANISM: Streptococcus mutans

<400> SEQUENCE: 5

Phe Ile Arg Ala His Asp Asn Asn Val Gln Asp Ile Ile Ala Glu Ile
1               5                   10                  15

Ile Lys Lys Glu Ile
            20

<210> SEQ ID NO 6
<211> LENGTH: 21
<212> TYPE: PRT
<213> ORGANISM: Streptococcus salivarius

<400> SEQUENCE: 6

Phe Ala Arg Ala His Asp Ser Glu Val Gln Asp Leu Ile Arg Asp Ile
1               5                   10                  15

Ile Lys Ala Glu Ile
            20

<210> SEQ ID NO 7
<211> LENGTH: 21
<212> TYPE: PRT
<213> ORGANISM: Streptococcus mutans

<400> SEQUENCE: 7

Phe Ile Arg Ala His Asp Ser Glu Val Gln Thr Val Ile Ala Lys Ile
1               5                   10                  15

Ile Lys Ala Gln Ile
            20

<210> SEQ ID NO 8
<211> LENGTH: 21
<212> TYPE: PRT
<213> ORGANISM: Streptococcus salivarius

<400> SEQUENCE: 8

Phe Ile Arg Ala His Asp Ser Glu Val Gln Thr Arg Ile Ala Lys Ile
1               5                   10                  15

Ile Arg Glu Lys Leu
            20

<210> SEQ ID NO 9
<211> LENGTH: 21
<212> TYPE: PRT
<213> ORGANISM: Leuconostoc mesenteroides

<400> SEQUENCE: 9

Phe Val Arg Ala His Asp Ser Glu Val Gln Thr Val Ile Ala Gln Ile
1               5                   10                  15

Val Ser Asp Leu Tyr
            20

<210> SEQ ID NO 10
<211> LENGTH: 21
<212> TYPE: PRT
<213> ORGANISM: Leuconostoc mesenteroides

<400> SEQUENCE: 10

Phe Val Arg Ala His Asp Ser Glu Val Gln Thr Val Ile Ala Glu Ile
1               5                   10                  15
```

Ile Lys Gln Arg Ile
            20

<210> SEQ ID NO 11
<211> LENGTH: 1514
<212> TYPE: PRT
<213> ORGANISM: Leuconostoc mesenteroides

<400> SEQUENCE: 11

Met Arg Asn Arg Asn Ala Thr Ser Val Phe Arg Lys Lys Met Tyr Lys
1               5                   10                  15

Ser Gly Lys Met Leu Val Ile Ala Gly Ser Val Ser Ile Ile Gly Val
            20                  25                  30

Thr Ser Phe Ile Gln Gln Ala Gln Ala Asp Val Ser Gln Asn Asn Gly
        35                  40                  45

Val Val Val Ala Thr Ala Val Asp Gln Ser Asn Leu Asp Ala Thr Thr
    50                  55                  60

Ser Asp Lys Ser Ile Thr Thr Asp Lys Ala Ala Thr Thr Ala Ala
65                  70                  75                  80

Thr Ser Thr Asp Asp Lys Ala Thr Thr Thr Val Ala Thr Ser Thr Asp
                85                  90                  95

Asp Lys Asp Thr Thr Thr Ala Ala Thr Ser Thr Asp Asp Lys Ala Thr
                100                 105                 110

Thr Thr Val Ala Thr Ser Thr Asp Asp Lys Ala Thr Thr Thr Ala Ala
            115                 120                 125

Thr Ser Thr Asp Asp Lys Ala Ala Thr Ala Ala Thr Ser Thr Asp
        130                 135                 140

Asp Lys Ala Ala Thr Ala Ala Thr Ser Thr Asp Asp Lys Ala Ala
145                 150                 155                 160

Thr Thr Ala Asp Thr Ser Thr Asp Lys Ala Ala Thr Thr Ala Ala
                165                 170                 175

Thr Ser Thr Asp Asp Lys Ala Thr Thr Thr Ala Ala Thr Ser Thr Asp
            180                 185                 190

Asp Lys Thr Ala Thr Thr Val Gly Thr Ser Asp Asn Asn Asn Ser Ala
        195                 200                 205

Thr Ala Ser Asp Lys Asp Val Ser Ser Ala Gln Lys Ser Gln Thr
    210                 215                 220

Ile Asp Asn Asn Ser Lys Thr Ala Asp Thr Thr Ala Ala Leu Glu Ala
225                 230                 235                 240

Ser Ser Lys Asn Leu Lys Thr Ile Asp Gly Lys Thr Tyr Tyr Tyr Asp
                245                 250                 255

Asp Asp Asp Gln Val Lys Lys Asn Phe Ala Thr Val Ile Asp Gly Lys
                260                 265                 270

Val Leu Tyr Phe Asp Lys Glu Thr Gly Ala Leu Ala Asp Thr Asn Asp
            275                 280                 285

Tyr Gln Phe Leu Glu Gly Leu Thr Ser Glu Asn Asn Thr Tyr Thr Glu
        290                 295                 300

His Asn Ala Ser Val Gly Thr Ser Ser Asp Ser Tyr Thr Asn Val Asp
305                 310                 315                 320

Gly Tyr Leu Thr Ala Asp Ser Trp Tyr Arg Pro Lys Asp Ile Leu Val
                325                 330                 335

Asn Gly Gln Asn Trp Glu Ser Ser Lys Asp Asp Leu Arg Pro Leu
            340                 345                 350

Leu Met Thr Trp Trp Pro Asp Lys Ala Thr Gln Val Asn Tyr Leu Asn
        355                 360                 365

```
Ala Met Lys Tyr Leu Asp Ala Thr Glu Thr Glu Thr Val Tyr Thr Ser
    370                 375                 380

Asp Asp Ser Gln Asp Ala Leu Asn Lys Ala Ala Gln Asn Ile Gln Val
385                 390                 395                 400

Lys Ile Glu Glu Lys Ile Ser Gln Glu Gly Gln Thr Gln Trp Leu Lys
                405                 410                 415

Asp Asp Ile Ser Lys Phe Val Asp Ser Gln Ser Asn Trp Asn Ile Ala
                420                 425                 430

Ser Glu Ser Lys Gly Thr Asp His Leu Gln Gly Ala Leu Leu Tyr
            435                 440                 445

Val Asn Ser Asp Lys Thr Pro Asp Ala Asn Ser Asp Tyr Arg Leu Leu
    450                 455                 460

Asn Arg Thr Pro Thr Asn Gln Thr Gly Thr Pro Leu Tyr Thr Thr Asp
465                 470                 475                 480

Pro Thr Gln Gly Gly Tyr Asp Phe Leu Leu Ala Asn Asp Val Asp Asn
                485                 490                 495

Ser Asn Pro Val Val Gln Ala Glu Gln Leu Asn Trp Met Tyr Tyr Leu
                500                 505                 510

Leu Asn Phe Gly Ser Ile Thr Asn Asn Asp Ala Asp Ala Asn Phe Asp
                515                 520                 525

Ser Ile Arg Val Asp Ala Val Asp Asn Val Asp Ala Asp Leu Leu Gln
            530                 535                 540

Ile Ala Ala Asp Tyr Phe Lys Ala Ala Tyr Gly Val Asp Lys Ser Asp
545                 550                 555                 560

Ala Ile Ser Asn Gln His Val Ser Ile Leu Glu Asp Trp Ser Asp Asn
                565                 570                 575

Asp Ala Glu Tyr Val Lys Asp Asn Gly Asp Asn Gln Leu Ser Met Asp
            580                 585                 590

Asn Lys Leu Arg Leu Ser Leu Lys Tyr Ser Leu Thr Met Pro Ala Val
            595                 600                 605

Asp Gln Tyr Gly Asn Lys Arg Ser Gly Leu Glu Pro Phe Leu Thr Asn
    610                 615                 620

Ser Leu Val Asp Arg Thr Asn Asp Ser Thr Asp Asn Thr Ala Gln Pro
625                 630                 635                 640

Asn Tyr Ser Phe Val Arg Ala His Asp Ser Glu Val Gln Thr Val Ile
                645                 650                 655

Ala Glu Ile Ile Lys Gln Arg Ile Asp Pro Asp Ser Asp Gly Leu Ser
                660                 665                 670

Pro Thr Met Asp Gln Leu Thr Glu Ala Phe Lys Ile Tyr Asn Ala Asp
            675                 680                 685

Gln Leu Lys Thr Asp Lys Glu Phe Thr Gln Tyr Asn Ile Pro Ser Thr
    690                 695                 700

Tyr Ala Thr Ile Leu Thr Asn Lys Asp Thr Val Pro Arg Val Tyr Tyr
705                 710                 715                 720

Gly Asp Met Tyr Thr Asp Asp Gly Gln Tyr Met Ala Thr Lys Ser Leu
                725                 730                 735

Tyr Tyr Asp Ala Ile Asp Thr Leu Leu Lys Ser Arg Ile Lys Tyr Val
            740                 745                 750

Ser Gly Gly Gln Thr Met Ser Met Lys Tyr Met Gln Gly Asp Ser Ser
        755                 760                 765

Met Ala Ala Asp Ser Tyr Arg Gly Ile Leu Thr Ser Val Arg Tyr Gly
    770                 775                 780
```

```
Asn Gly Ala Met Thr Ala Thr Asp Ala Gly Thr Asn Glu Thr Arg Thr
785                 790                 795                 800

Gln Gly Ile Ala Val Ile Glu Ser Asn Asn Pro Asp Leu Lys Leu Ser
            805                 810                 815

Ser Thr Asp Gln Val Val Asp Met Gly Ile Ala His Lys Asn Gln
        820                 825                 830

Ala Tyr Arg Pro Ala Leu Leu Thr Thr Lys Asp Gly Ile Asp Thr Tyr
        835                 840                 845

Val Ser Asp Ser Asp Val Ser Gln Ser Leu Ile Arg Tyr Thr Asn Ser
850                 855                 860

Asn Gly Gln Leu Ile Phe Asn Ser Ser Asp Ile Val Gly Thr Ala Asn
865                 870                 875                 880

Pro Gln Val Ser Gly Tyr Leu Ala Val Trp Val Pro Val Gly Ala Ser
            885                 890                 895

Asp Thr Gln Asp Ala Arg Thr Glu Ser Ser Thr Ala Thr Thr Ala Asp
            900                 905                 910

Gly Gln Thr Leu His Ser Asn Ala Ala Leu Asp Ser Val Ile Tyr
        915                 920                 925

Glu Ser Phe Ser Asn Phe Gln Ser Thr Pro Thr Thr Glu Ala Glu Tyr
930                 935                 940

Ala Asn Val Gln Ile Ala Asn Asn Thr Asp Leu Tyr Lys Ser Trp Gly
945                 950                 955                 960

Ile Thr Asn Phe Glu Phe Pro Pro Gln Tyr Arg Ser Ser Thr Asp Ser
                965                 970                 975

Ser Phe Leu Asp Ser Ile Ile Gly Asn Gly Tyr Ala Phe Thr Asp Arg
            980                 985                 990

Tyr Asp Leu Gly Phe Asn Thr Pro  Thr Lys Tyr Gly Thr  Val Asp Gln
        995                 1000                1005

Leu Arg  Thr Ala Ile Lys Ala  Leu His Ala Thr Gly  Ile Lys Ala
    1010            1015                1020

Met Ala  Asp Trp Val Pro Asp  Gln Ile Tyr Asn Leu  Thr Gly Lys
    1025            1030                1035

Glu Val  Val Ala Val Gln Arg  Val Asn Asn Ser Gly  Ile Tyr Asn
    1040            1045                1050

Gln Asp  Ser Val Ile Asn Lys  Thr Leu Tyr Ala Ser  Gln Thr Val
    1055            1060                1065

Gly Gly  Gly Glu Tyr Gln Ala  Leu Tyr Gly Gly Glu  Phe Leu Asp
    1070            1075                1080

Glu Ile  Lys Lys Leu Tyr Pro  Ser Leu Phe Glu Lys  Asn Gln Ile
    1085            1090                1095

Ser Thr  Gly Val Pro Met Asp  Ala Ser Glu Lys Ile  Lys Glu Trp
    1100            1105                1110

Ser Ala  Lys Tyr Phe Asn Gly  Thr Asn Ile Gln Gly  Arg Gly Ala
    1115            1120                1125

Tyr Tyr  Val Leu Lys Asp Trp  Ala Thr Asn Glu Tyr  Phe Lys Val
    1130            1135                1140

Ser Thr  Ser Ser Asn Ser Ser  Val Phe Leu Pro Lys  Gln Leu Thr
    1145            1150                1155

Asn Glu  Glu Ser Asn Thr Gly  Phe Ile Ser Thr Asp  Gly Gly Met
    1160            1165                1170

Thr Tyr  Tyr Ser Thr Ser Gly  Tyr Gln Ala Lys Asp  Thr Phe Ile
    1175            1180                1185

Gln Asp  Asp Lys Ser Asn Trp  Tyr Tyr Phe Asp Lys  Asn Gly Tyr
```

-continued

```
                   1190                     1195                     1200
Met  Thr  Tyr  Gly  Phe  Gln  Thr  Val  Asn  Asp  Asn  Tyr  Tyr  Phe
     1205                     1210                     1215

Leu  Pro  Asn  Gly  Ile  Glu  Leu  Gln  Asp  Ala  Ile  Leu  Glu  Asp  Ser
     1220                     1225                     1230

Lys  Gly  Asn  Val  Tyr  Tyr  Phe  Asn  Gln  Tyr  Gly  Lys  Gln  Ala  Val
     1235                     1240                     1245

Asp  Gly  Tyr  Tyr  Met  Leu  Ala  Asn  Lys  Thr  Trp  Arg  Tyr  Phe  Asp
     1250                     1255                     1260

Lys  Asn  Gly  Val  Met  Ala  Asn  Ala  Gly  Leu  Thr  Thr  Val  Thr  Val
     1265                     1270                     1275

Asp  Gly  Gln  Glu  His  Ile  Gln  Tyr  Phe  Asp  Lys  Asn  Gly  Ile  Gln
     1280                     1285                     1290

Val  Lys  Gly  Thr  Ser  Val  Lys  Asp  Ala  Asp  Gly  Lys  Leu  Arg  Tyr
     1295                     1300                     1305

Phe  Asp  Thr  Asp  Ser  Gly  Asp  Met  Val  Thr  Asn  Arg  Phe  Gly  Glu
     1310                     1315                     1320

Asn  Thr  Asp  Gly  Thr  Trp  Ser  Tyr  Phe  Gly  Ala  Asp  Gly  Ile  Ala
     1325                     1330                     1335

Val  Thr  Gly  Ala  Gln  Thr  Ile  Ser  Gly  Gln  Lys  Leu  Phe  Phe  Asp
     1340                     1345                     1350

Ala  Asp  Gly  Gln  Gln  Ile  Lys  Gly  Lys  Glu  Ala  Thr  Asp  Lys  Lys
     1355                     1360                     1365

Gly  Lys  Val  His  Tyr  Tyr  Asp  Ala  Asn  Ser  Gly  Glu  Met  Ile  Thr
     1370                     1375                     1380

Asn  Arg  Phe  Glu  Lys  Leu  Ser  Asp  Gly  Ser  Trp  Ala  Tyr  Phe  Asn
     1385                     1390                     1395

Lys  Lys  Gly  Asn  Ile  Val  Thr  Gly  Ala  Gln  Val  Ile  Asn  Gly  Gln
     1400                     1405                     1410

His  Leu  Phe  Phe  Glu  Ser  Asn  Gly  Asn  Gln  Val  Lys  Gly  Arg  Glu
     1415                     1420                     1425

Tyr  Thr  Ala  Thr  Asp  Gly  Lys  Met  Arg  Tyr  Tyr  Asp  Ala  Asp  Ser
     1430                     1435                     1440

Gly  Asp  Met  Val  Thr  Asn  Arg  Phe  Glu  Arg  Ile  Ser  Asp  Gly  Ser
     1445                     1450                     1455

Trp  Ala  Tyr  Phe  Gly  Ala  Asn  Gly  Val  Ala  Val  Thr  Gly  Glu  Gln
     1460                     1465                     1470

Asn  Ile  Asn  Gly  Gln  Gln  Leu  Tyr  Phe  Asp  Ala  Asn  Gly  His  Gln
     1475                     1480                     1485

Val  Lys  Gly  Ala  Ala  Val  Thr  Gln  Ala  Asp  Gly  Ser  Gln  Lys  Tyr
     1490                     1495                     1500

Tyr  Asp  Ala  Asn  Ser  Gly  Glu  Met  Ile  Lys  Ser
     1505                     1510
```